(12) United States Patent
Bertola

(10) Patent No.: US 6,248,906 B1
(45) Date of Patent: Jun. 19, 2001

(54) PROCESS FOR THE PRODUCTION OF TETRAHYDROFURAN, GAMMABUTYROLACTONE AND BUTANEDIOL

(76) Inventor: Aldo Bertola, Via Luigi Illica, 5 - 20121 Milan (IT)

( * ) Notice: Subject to any disclaimer, the term of this patent is extended or adjusted under 35 U.S.C. 154(b) by 0 days.

(21) Appl. No.: 09/367,045

(22) PCT Filed: Jan. 5, 1999

(86) PCT No.: PCT/EP99/00014

§ 371 Date: Aug. 6, 1999

§ 102(e) Date: Aug. 6, 1999

(87) PCT Pub. No.: WO99/35113

PCT Pub. Date: Jul. 15, 1999

(30) Foreign Application Priority Data

Jan. 8, 1998 (BE) .................................................. 9800012

(51) Int. Cl.⁷ ..................... C07D 307/33; C07D 307/08; C07C 29/149

(52) U.S. Cl. .......................... 549/326; 549/508; 568/864

(58) Field of Search .................................... 549/326, 508; 568/864

(56) References Cited

U.S. PATENT DOCUMENTS

| 2,251,895 | 8/1941 | Reppe et al. | 549/509 |
|---|---|---|---|
| 4,032,458 | 6/1977 | Cooley et al. | 549/508 |
| 4,584,419 | 4/1986 | Sharif et al. . | |
| 4,652,685 | 3/1987 | Cawse et al. | 549/508 |
| 4,751,334 | 6/1988 | Turner et al. . | |
| 5,792,875 | * 8/1998 | Chaudhari et al. | 549/326 |

FOREIGN PATENT DOCUMENTS

| 892958 | 8/1982 | (BE) . |
|---|---|---|
| 0190424 | 8/1986 | (EP) . |
| 8603189 | 6/1986 | (WO) . |

* cited by examiner

*Primary Examiner*—Bernard Dentz
(74) *Attorney, Agent, or Firm*—Stevens, Davis, Miller & Mosher, LLP

(57) ABSTRACT

Process for the production of tetrahydrofuran, gammabutyrolactone and butanediol starting from maleic anhydride esters, consisting of two subsequent hydrogenations.

23 Claims, 2 Drawing Sheets

PROCESS FOR THE PRODUCTION OF TETRAHYDROFURAN, GAMMABUTYROLACTONE AND BUTANEDIOL

This is a 371 of PCT/EP99/00014 filed Jan. 5, 1999.

The present invention relates to a process for the production of tetrahydrofuran, gammabutyrolactone and butanediol starting from maleic anhydride esters, consisting of two subsequent hydrogenations.

It is known that tetrahydrofuran (THF), gammabutyrolactone (GBL) and butanediol (BDO) can be produced thanks to several methodologies. THF and GBL are chiefly produced starting from BDO. THF is produced starting from butanediol (BDO) by a dehydrogenation process.

THF and GBL production from BDO results to be expensive, because of the relatively high costs arising from the BDO production processes, inherently rather complex.

According to a technique employed in industry, BDO is produced by reaction of acetylene with formaldehyde, with ensuing formation of butanediol, which itself undergoes hydrogenation to BDO.

Mitsubishi Chemical Industries developed a process apt at producing BDO with Butadiene as starting material.

The process involves butadiene acetoxylation to 1,4-diacetoxy-2-butene, that is then hydrogenated and hydrolised to BDO.

General Electric Corp. patented a process for the production of BDO starting from propylene.

The process includes the conversion of propylene to allyl acetate, which is converted into 4-acetoxybutanol. This eventually hydrolyses to afford BDO.

A special attention has been devoted to the development of processes where butane is employed as starting material, via the formation of a maleic anhydride intermediate.

Several processes have been proposed for the production of THF, GBL and BDO starting from maleic anhydride, esters thereof, or homologous compounds such as succinic acid and/or fumaric acid esters.

In U.S. Pat. Nos. 4,584,419 and 4,751,334 in the name of Davy MeKee Ltd., processes are described for the production of BDO by hydrogenation of carboxylic acid esters containing 4 Carbon atoms, typically ethyl maleate.

In the above patents, claims refer to hydrogenations carried out within a field with pressures ranging between 25 and 75 bars, and temperatures between 150 and 240° C., in the presence of a stabilised copper chromite type catalyst.

An aim of the present invention is to provide a process whereby THF and GBL can be produced in variable proportions by hydrogenation at moderate pressures with maleic anhydride esters as starting materials, without going through BDO production.

BDO can be produced starting from GBL by subsequent hydrogenation carried out at a higher pressure.

It is another aim of the present invention that of proposing a more straightforward process with higher final product yields, without the need to resort to the extreme pressure and temperature conditions which are proper of the processes proposed in the prior art.

According to the invention the above aims are accomplished thanks to a process for the production of tetrahydrofuran, gamma butyrolactone and butanediol with maleic anhydride esters as starting materials, by two successive hydrogenations.

More particularly the process comprises:
a) A primary hydrogenation of maleic anhydride ester in the vapour phase, at a moderate pressure, in a reactor comprising three reaction stages connected in series.

In the first of the stages thereof a heterogeneous selective hydrogenation catalyst is employed to carry out a conversion of maleic anhydride ester into succinic anhydride ester.

In the second stage a selective hydrogenation catalyst is employed to carry out a conversion of succinic anhydride ester mainly into GBL.

In the third stage of dehydration catalyst is employed mainly to produce THF.

b) Separation of the effluent from the primary from THF and GBL products.

c) Feeding a fraction of the GBL produced to a secondary hydrogenation in the vapour phase and at a higher pressure, on a hydrogenation catalyst where GBL is mainly converted to BDO.

These and other features will be more readily apparent from the following description of a preferred not limiting embodiment of the invention with reference to the accompanying drawings in which.

In the process object of the present invention, maleic anhydride ester, preferably dimethymaleate (DMM) is completely vapourised in a hydrogen rich stream, to be fed to a reaction system containing three distinct catalysts connected in series. The reaction system thereabout is hereafter indicated as primary hydrogenation.

The first stage of the primary hydrogenation employs a noble metal based heterogeneous selective hydrogenation catalyst.

In the second stage of the primary hydrogenation a heterogeneous copper-zinc oxide or copper chromite type catalyst is employed.

In the third stage of the primary hydrogenation, a silica-alumina type heterogeneous catalyst is employed. This is acidic and rich in silica.

To allow the reaction to occur in the vapour phase, it is necessary that the reaction mixture be rich in hydrogen.

The $H_2$ to ester molar ratio in the three stages of the primary hydrogenation reactor ranges between 50 and 600, preferably between 70 and 200.

Pressure and temperature in the primary hydrogenation, as well as residence times on the catalysts can be optimised depending on the proportions between the GBL and THF to be produced.

The above ratio can be varied within a large interval, which spans between the 90:10 and the 10:90 GBL:THF ratios.

Optimal overall yields are obtained operating the reaction with the ratios of the above ranging between 70:30 and 40:60.

The overall average operating pressure ranges between 3 and 40 bars, and preferably between 15 and 25 bars.

Temperature at the inlet of the first reaction stage is between 120 and 170° C., preferably between 190° and 220° C.

Liquid Hourly Space Velocity in the first stage ranges between 1.0 and 3.0 $hr^{-1}$.

Liquid Hourly Space Velocity in the second and third stages range between 1.0 and 0.5 $hr^{-1}$.

The space velocity with which the gaseous mixture flows on the catalyst of the third reaction stage results to be 1.5 to 10 times higher than that it has when it flows on the catalyst of the second stage.

A cooling between the several reaction stages can be carried out by admixing a cold hydrogen stream to the effluent from the previous stage of reaction.

Figure 1:
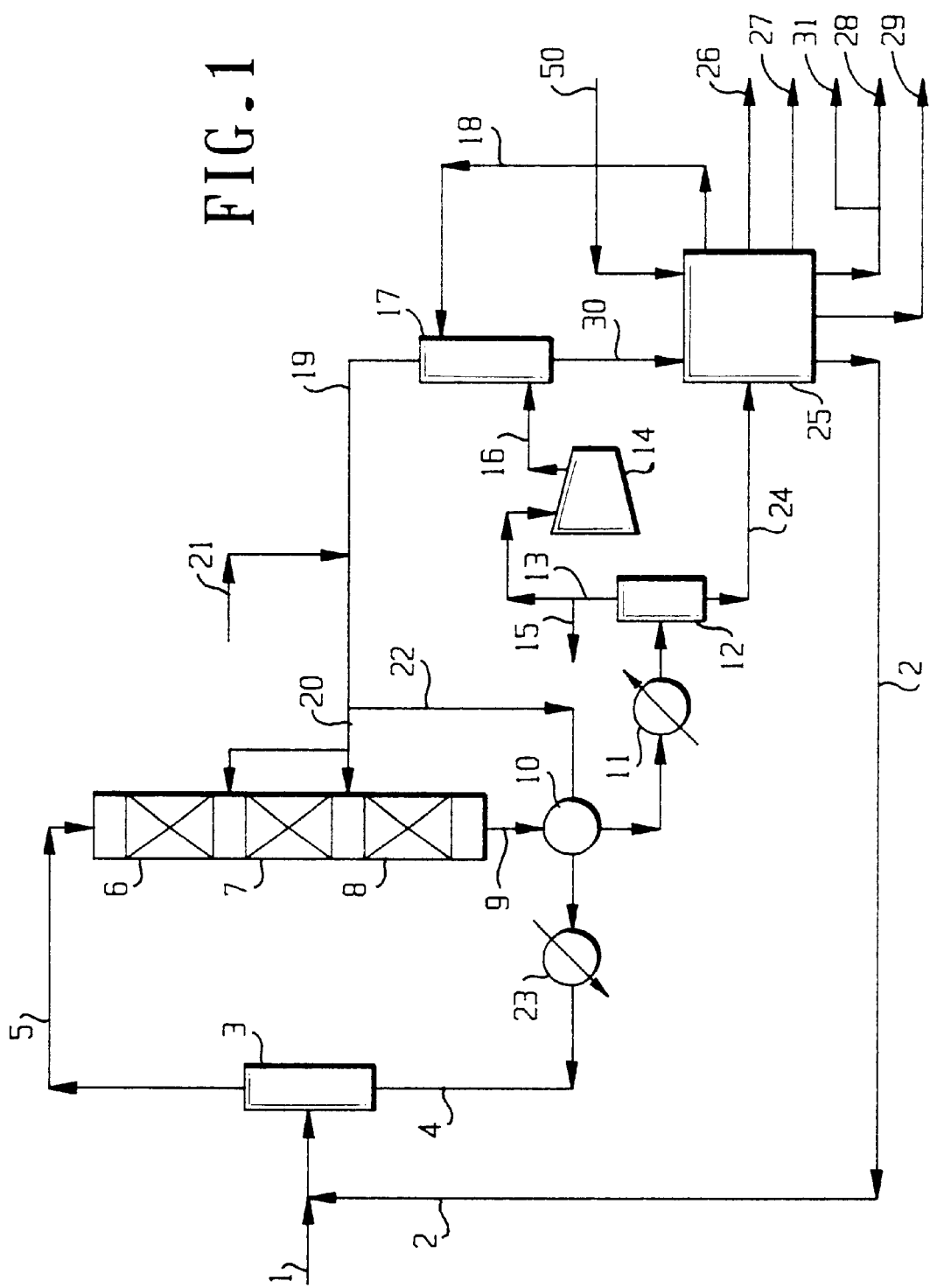
FIG. 1 shows the typical scheme for the primary hydrogenation.

The typical scheme of the primary hydrogenation process is given in FIG. 1. Operating conditions refer to dimethylmaleate (DMM) as starting material.

Essentially, the process holds even in case the starting material is made up of other maleic anhydride esters.

The ester feedstock (line 1) is fed to vapouriser 3 together with a recycle stream (line 2) containing BDO and unconverted dimethylsuccinate (DMS), from product fractionation unit 25.

In the recycle stream GBL is also typically present, and this forms an azeotrope with DMS.

In vapouriser 3 the feedstock (line 1) and the recycle (line 2) come to contact with a hot hydrogen stream (line 4) and they vapourise.

In the gas stream at the outlet of the vapouriser (line 5), the $H_2$ to shot molar ratio is 100, temperature is 140° C., pressure is 15 ATE.

Such stream feeds the first stage of hydrogenation 6 that contains a heterogeneous selective hydrogenation catalyst which is typically, and not limitedly, of the palladium on alumina type.

In the first reaction stage DMM is fully hydrogenated to DMS.

The effluent feeds into the second stage of reaction 7 where a copper-zinc oxide or stabilised copper chromite type catalyst is contained.

At the outlet of the second reaction stage, temperature is taken down from approximately 325 to approximately 200° C. by injection of a cold hydrogen stream (line 20).

In the third stage of reaction 8, gases flow onto an acidic catalyst of the silica-alumina type. Mordenites or acidic zeolites are one type of catalyst employed in the process. There have an 0.65 ABD apparent density and a 450 $m^2gr^{-1}$ surface area.

At the outlet of the third reaction stage, the overall conversion is as high as 97% and product distribution is the following:

| | | |
|---|---|---|
| GBL: | | 53% |
| THF: | | 34% |
| BDO: | | 7% |
| Byproducts: | | 3% |

Overall Liquid Hourly Space Velocity in the first reaction stage is 2.5 $hr^{-1}$. Overall Liquid Hourly Space Velocity in the second and third reaction stages is 0.2 $hr^{-1}$.

The effluent from the third reaction stage (line 9) cools down in exchanger 10 letting off heat to the recycle hydrogen stream. It also does so in exchanger 11 and eventually feeds separator 12 where the condensed organic phase and the hydrogen enriched gaseous phase separate.

After leaving separator 12, the gaseous phase (line 13) is compressed in compressor 14, and is then recycled to the reaction system. A fraction of recycle gas is purged (line 15) to avoid excessive deposition of inert materials.

Compressed gas feeds (line 16) column 17, where it comes to contact with a GBL enriched stream (line 18) from product fractionation unit 25, which washes it. This allows removal of the steam present in the gases.

As known, water is a common byproduct in THF synthesis.

Such an effective removal of water as that achieved washing recycle gases with a GBL enriched liquid stream is important to avoid deterioration of the copper based catalyst.

After washing, the GBL enriched stream (line 30) returns to the byproduct fractionation unit 25 where the absorbed water is removed.

Dried gases (line 19) together with the hydrogen feedstock, partly mix with the effluents from reactors 6 and 7 for temperature check, and partly (line 22) preheat in exchanger 10 and subsequently in exchanger 23, where THF (line 26), water, methanol light organic byproducts (line 27), GBL (line 28), a fraction containing BDO and DMS which is eventually recycled into the reaction (line 2) and heavy organic byproducts (line 29) separate.

A fraction of the GBL produced (line 31) is fed to the subsequent hydrogenation unit hereafter known as secondary hydrogenation, which operates at high pressure.

The following are the typical operating conditions of the secondary reaction at the reactor inlet in the process object of the present invention:

| | |
|---|---|
| Reaction Type: | adiabatic |
| Hydrogen:ester molar ratio | from 100 to 800, preferably from 200 to 800. |
| Operating Pressure: | from 75 to 120 bars, preferably from 80 to 100 bars |
| Operating emperature: | from 160° to 230° C., preferably from 190° to 210° C. |
| Catalyst Type: | Copper-Zinc oxid or copper chromite. |
| Liquid Hourly Space Velocity: | from 0.1 to 1.0 $hr^{-1}$, averagely from 0.3 to 0.5 $hr^{-1}$. |

Figure 2:
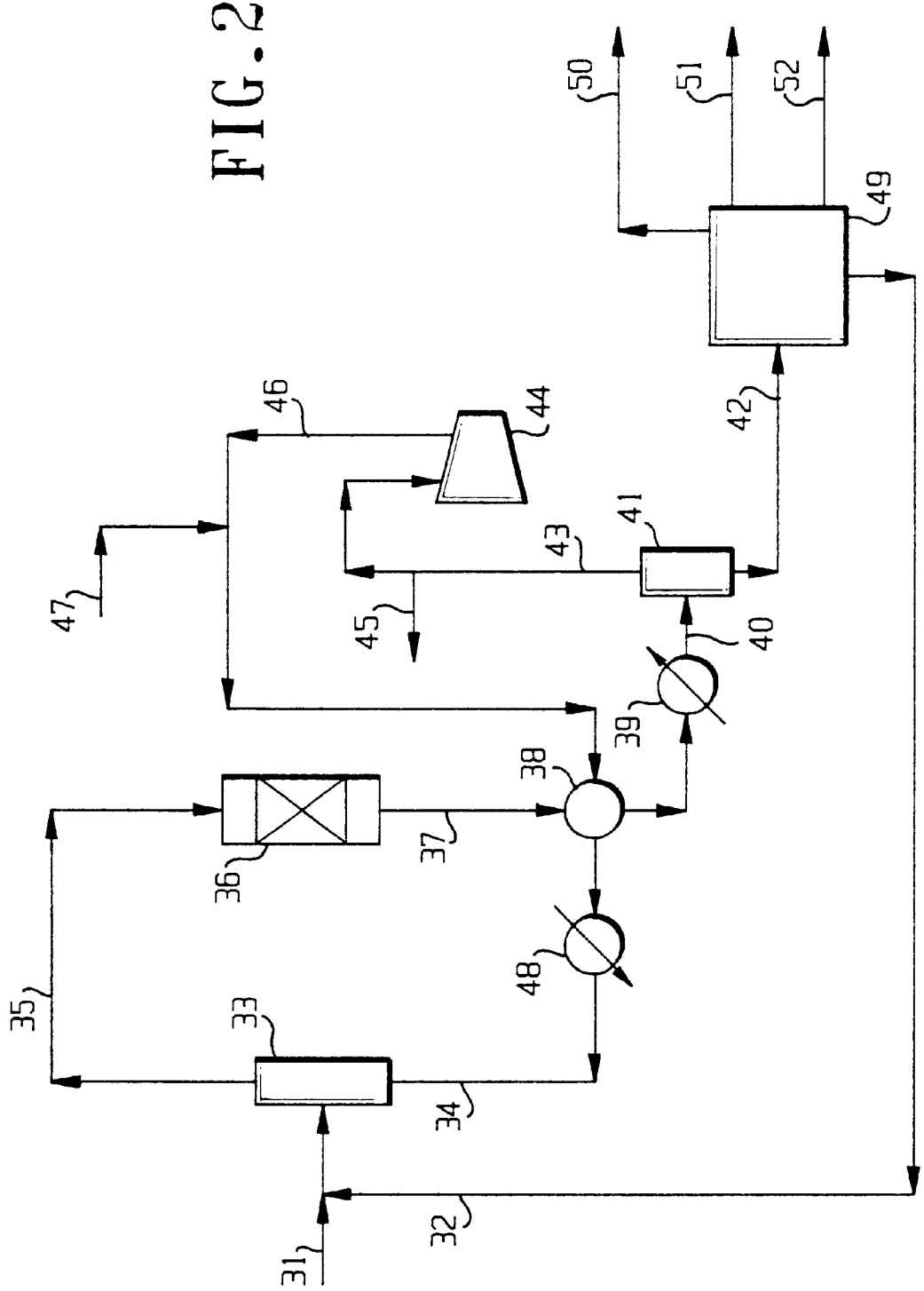
FIG. 2 shows a typical scheme for the secondary hydrogenation.

A scheme of the secondary hydrogenation is given in FIG. 2.

GBL feedstock (line 31), together with a liquid recycle stream (line 32) containing GBL from fractionation unit 49, is fed to vapouriser 33. Therein the shot (line 31) and the recycle (line 32) come to contact with a hot hydrogen stream (line 34) and vapourise.

At the vapouriser outlet, temperature is 190° C., pressure is 80 ATE and the gas stream (line 35) has a hydrogen to ester ratio equalling 300:1.

Such gas stream feeds reactor 36 where a catalyat of the copper-zinc oxide type or stabilised copper chromite type catalyst is contained. The latter has a surface area which is never any lower than 40 $m^2g^{-1}$.

Liquid Hourly Space Velocity is 0.35 $hr^{-1}$. At the reactor outlet, more than 90% of the GBL feedstock has been converted.

Tetrahydrofuran is obtained as a byproduct and it totals up to 6% of the overall GBL produced, on a molar basis.

The reaction shows a ca. 99% selectivity with respect to the total BDO plus THF produced.

The effluent from the reactor (line 37) cools down in exchanger 38, where it gives off heat to the hydrogen enriched stream. After that it cools down in exchanger 39, before feeding into separator 41 (line 40), where the condensed organic phase separates from the hydrogen enriched gaseous phase.

After leaving separator 41 (line 43), the gaseous phase is compressed in compressor 44, before being recycled to the reaction system.

A small fraction of the recycle gas is purged (line 45) to avoid excessive accumulation of inert material.

Compressed gas (line 46) admixes to the feed hydrogen (line 47) and preheats in exchanger 38 as well as in terminal heater 48. After that it feeds (line 34) vapouriser 33.

After leaving separator 41, the liquid phase feeds (line 42) product fractionation unit 49 where two products are separated: one consisting of THF, water and light organic byproducts, which is directed (line 50) towards the THF recovery unit. The other is an unconverted GBL enriched fraction (line 32) and it is recycled to hydrogenation. Heavy organic byproducts (line 51) and BDO (line 52) separate at the same time.

The entire process thereof allows production of THF, GBL and BDO directly and with a high degree of flexibility, avoiding all the complications presented by all those processes where THF and GBL are produced using BDO as starting material.

What is claimed is:

1. A process for the production of tetrahydrofuran, gamma butyrolactone and butanediol with maleic anhydride esters as starting materials, characterised in that it comprises a sequence of the following three steps: a step wherein a primary hydrogenation of maleic anhydride ester is carried out; a step wherein the effluent originated in the primary hydrogenation is separated from the products, namely GBL and THF; a step wherein a fraction of the GBL produced is fed to a secondary hydrogenation reaction where GBL is mainly converted to BDO using as starting materials maleic anhydride esters where the alkyl component has from 1 to 4 carbon atoms, wherein it comprises a sequence of two hydrogenations in series:

the primary hydrogenation comprises three reaction stages in series, wherein: in the first of said stages the maleic anhydride ester is converted into succinic anhydride ester; in the second of said stages the succinic anhydride ester is mainly converted into GBL; in the third of said stages mainly THF is produced; and in the secondary hydrogenation a fraction of GBL produced in the primary hydrogenation is converted to BDO.

2. A process according to claim 1, wherein the primary hydrogenation of maleic anhydride ester takes place in the vapor phase and at an operating pressure that ranges between 3 and 40 bar and at an operating temperature that ranges between 120 and 250° C.

3. A process according to claim 1, wherein the reaction of the first stage occurs on a heterogeneous selective noble metal based hydrogenation catalyst, the reaction of the second stage occurs on a heterogeneous selective hydrogenation catalyst, and the reaction of the third stage occurs on a heterogeneous dehydration catalyst.

4. Process according to claim 1, wherein the secondary hydrogenation takes place in the vapor phase and at a pressure which is higher than that of the primary hydrogenation.

5. A process according to claim 1, wherein all along the three stages of the primary hydrogenation, the molar ratio between hydrogen and ester ranges between 50 and 600.

6. A process according to claim 3, wherein the molar ratio between hydrogen and ester in all three stages of the primary hydrogenation ranges between 70 and 200.

7. A process according to claim 1, wherein the ratio between the GBL and THF products ranges between 10:90 and 90:10.

8. A process according to claim 7, wherein the ratio between the GBL and THF products ranges between 70:30 and 40:60.

9. A process according to claim 2, wherein the Liquid Hourly Space Velocity in the first stage ranges between 1 and 3 $hr^{-1}$.

10. A process according to claim 2 wherein the Liquid Hourly Space Velocity in the second stage ranges between 0.1 and 0.5 $hr^{-1}$.

11. A process according to claim 2, wherein the catalyst in the third stage has a specific surface ranging between 50 and 800 $m^2g^{-1}$.

12. A process according to claim 2 wherein the catalyst in the third stage contains between 60 and 100% silica.

13. A process according to claim 1, wherein the alkyl component of the maleic anhydride ester consists of 1 to 4 carbon atoms.

14. A process according to claim 1, wherein the primary hydrogenation is carried out at an operating pressure that range between 3 and 40 bars, and at an operating temperature that ranges between 120 and 250° C.

15. A process according to claim 1, wherein the catalyst at the first stage of the primary hydrogenation reactor is noble metal based, the catalyst at the second stage is a catalyst of the copper-zinc oxide or stabilized copper chromite type, the catalyst of the third stage is of the alumina-silica type, it is acidic and rich in silica.

16. A process according to claim 15, wherein the catalyst at the first stage of the primary hydrogenation reactor is Palladium on alumina substrate.

17. A process according to claim 1, wherein the Liquid Hourly Space Velocity in the first stage ranges between 1 and 3 $hr^{-1}$.

18. A process according to claim 1, wherein the Liquid Hourly Space Velocity in the second stage ranges between 0.1 and 0.5 $hr^{-1}$.

19. The process according to claim 3, wherein the reaction of the first stage occurs at a pressure between 15 and 25 bar.

20. The process according to claim 3, wherein the reaction of the first stage occurs on a noble metal based hydrogenation catalyst supported on an alumina substrate.

21. The process according to claim 3, wherein the hydrogenation catalyst of the second stage is a copper-zinc oxide or a stabilized copper chromite.

22. The process of claim 3, wherein the dehydration catalyst of the third stage is an acid silica-alumina catalyst, rich in alumina.

23. The process of claim 4, wherein the secondary hydrogenation which takes place in the vapor phase is in the presence of a copper-zinc oxide or copper chromite catalyst.

* * * * *